United States Patent
Hatton et al.

(10) Patent No.: US 9,580,214 B2
(45) Date of Patent: Feb. 28, 2017

(54) PORT CLOSURE SYSTEM FOR USE WITH A PROBE/FEED/DRAIN TOOL

(75) Inventors: Jason D. Hatton, Essexville, MI (US); David J. Gaus, Saginaw, MI (US); John Miller Hess, III, Midland, MI (US)

(73) Assignee: AptarGroup, Inc., Crystal Lake, IL (US)

( * ) Notice: Subject to any disclaimer, the term of this patent is extended or adjusted under 35 U.S.C. 154(b) by 80 days.

(21) Appl. No.: 14/111,824

(22) PCT Filed: May 4, 2011

(86) PCT No.: PCT/US2011/035191
§ 371 (c)(1),
(2), (4) Date: Oct. 15, 2013

(87) PCT Pub. No.: WO2012/150937
PCT Pub. Date: Nov. 8, 2012

(65) Prior Publication Data
US 2014/0224356 A1    Aug. 14, 2014

(51) Int. Cl.
*F16L 29/00*    (2006.01)
*B65D 47/20*    (2006.01)
(Continued)

(52) U.S. Cl.
CPC ....... *B65D 47/2031* (2013.01); *A61M 39/045* (2013.01); *A61M 2039/0072* (2013.01); *Y10T 137/7876* (2015.04)

(58) Field of Classification Search
CPC . B65D 81/261; B65D 47/2031; B65D 51/002
(Continued)

(56) References Cited

U.S. PATENT DOCUMENTS

| 1,825,553 A | 9/1931 | Smith |
| 3,621,876 A | 11/1971 | Campbell |

(Continued)

FOREIGN PATENT DOCUMENTS

| EP | 0 947 440 A1 | 10/1999 |
| FR | 996 998 | 12/1951 |

(Continued)

OTHER PUBLICATIONS

The "International Search Report and Written Opinion of the International Searching Authority, or the Declaration" dated Dec. 8, 2009 for International Application No. PCT/US2009/05751 claiming priority of U.S. Appl. No. 12/268,814, now U.S. Pat. No. 8,316,890.

(Continued)

*Primary Examiner* — Jessica Cahill
*Assistant Examiner* — Angelisa L Hicks
(74) *Attorney, Agent, or Firm* — Wood, Phillips, Katz, Clark & Mortimer

(57) ABSTRACT

A port closure system (20) including a retention structure (22), and a valve (24). The retention structure (22) includes a port (28) for establishing communication between an exterior environment (30) and interior volume (32) that can receive a fluent substance. The valve (24) includes a flexible, resilient, self-closing, slit-type valve head (36) with an orifice that is normally closed in an unconstrained condition. The port (28) has a laterally inwardly facing engaging surface (34) and the valve has a laterally outwardly facing peripheral surface (54) that is compressed laterally inwardly by engagement with the surface (34) to increase the resistance of the normally closed orifice to opening when the head (36) is subjected to a pressure differential. The system (20) further includes an annular flange (62) located to extend over at least a portion of an exterior side (38) of the valve (Continued)

head (36) to limit movement of the valve head (36) towards the exterior environment (30).

15 Claims, 7 Drawing Sheets

(51) Int. Cl.
*A61M 39/04* (2006.01)
*A61M 39/00* (2006.01)

(58) Field of Classification Search
USPC ............ 251/149, 149.2, 149.6, 149.7, 149.8
See application file for complete search history.

(56) References Cited

U.S. PATENT DOCUMENTS

| | | |
|---|---|---|
| 4,749,108 A | 6/1988 | Dornsbusch et al. |
| 4,909,798 A | 3/1990 | Fleischhacker et al. |
| 4,991,745 A | 2/1991 | Brown |
| 5,033,655 A | 7/1991 | Brown |
| 5,115,950 A | 5/1992 | Rohr |
| 5,213,236 A | 5/1993 | Brown et al. |
| 5,271,531 A | 12/1993 | Rohr et al. |
| 5,297,599 A | 3/1994 | Bucheli |
| 5,339,995 A | 8/1994 | Brown et al. |
| 5,377,877 A | 1/1995 | Brown et al. |
| 5,409,144 A | 4/1995 | Brown |
| 5,439,143 A | 8/1995 | Brown et al. |
| 5,531,363 A | 7/1996 | Gross |
| 5,676,289 A | 10/1997 | Gross et al. |
| 5,839,614 A | 11/1998 | Brown |
| 5,904,275 A | 5/1999 | Suffa |
| 5,927,566 A | 7/1999 | Mueller |
| 5,934,512 A | 8/1999 | Lampe et al. |
| 6,062,435 A | 5/2000 | Hess, III |
| 6,062,436 A | 5/2000 | Fuchs |
| 6,065,642 A | 5/2000 | Brown |
| 6,092,551 A | 7/2000 | Bennett |
| 6,112,951 A | 9/2000 | Mueller |
| 6,112,952 A | 9/2000 | Hess, III et al. |
| 6,131,806 A | 10/2000 | Hess, III et al. |
| 6,273,296 B1 | 8/2001 | Brown |
| 6,273,305 B1 * | 8/2001 | Fioravanti et al. ........... 222/494 |
| 6,293,437 B1 | 9/2001 | Socier et al. |
| 6,405,901 B1 | 6/2002 | Schantz et al. |
| 6,427,874 B2 | 8/2002 | Brown et al. |
| 6,530,504 B2 | 3/2003 | Socier |
| 6,616,016 B2 | 9/2003 | Hicks et al. |
| 6,951,295 B1 | 10/2005 | Gaus et al. |
| 6,971,558 B2 | 12/2005 | Ramsey et al. |
| 7,784,652 B2 | 8/2010 | Gaus et al. |
| 2004/0040987 A1 * | 3/2004 | Ramsey et al. ............... 222/490 |
| 2004/0232175 A1 * | 11/2004 | deCler et al. ................. 222/567 |
| 2005/0087555 A1 | 4/2005 | Hatton et al. |
| 2005/0269354 A1 * | 12/2005 | Smith ............................. 222/83 |
| 2005/0269373 A1 * | 12/2005 | Gaiser et al. ................. 222/494 |
| 2006/0249536 A1 | 11/2006 | Hartman et al. |
| 2007/0113855 A1 * | 5/2007 | Carlsen .................... 128/207.12 |
| 2007/0114250 A1 | 5/2007 | Langseder et al. |
| 2007/0251079 A1 * | 11/2007 | Pugne ............................. 29/428 |
| 2008/0035677 A1 | 2/2008 | Daansen |
| 2008/0066815 A1 | 3/2008 | Anderson |
| 2008/0237278 A1 | 10/2008 | Gaus et al. |
| 2009/0212078 A1 | 8/2009 | Gaus et al. |
| 2010/0116371 A1 | 5/2010 | Gaus |
| 2010/0193516 A1 | 8/2010 | LaBean et al. |

FOREIGN PATENT DOCUMENTS

| | | |
|---|---|---|
| JP | 50-32516 | 3/1975 |
| JP | 2-73151 | 2/1990 |
| WO | WO 98/14386 | 4/1998 |
| WO | WO 99/10247 | 3/1999 |

OTHER PUBLICATIONS

The "International Search Report and Written Opinion of the International Searching Authority, or the Declaration" dated Mar. 3, 2009 for International Application No. PCT/US2009/00501 claiming priority of U.S. Appl. No. 12/070,799.

The "International Search Report and Written Opinion of the International Searching Authority, or the Declaration" dated Aug. 11, 2012 for the International Application No. PCT/US2011/035191 of which the above-captioned instant U.S. Appl. No. 14/111,824 is a U.S. national phase application.

* cited by examiner

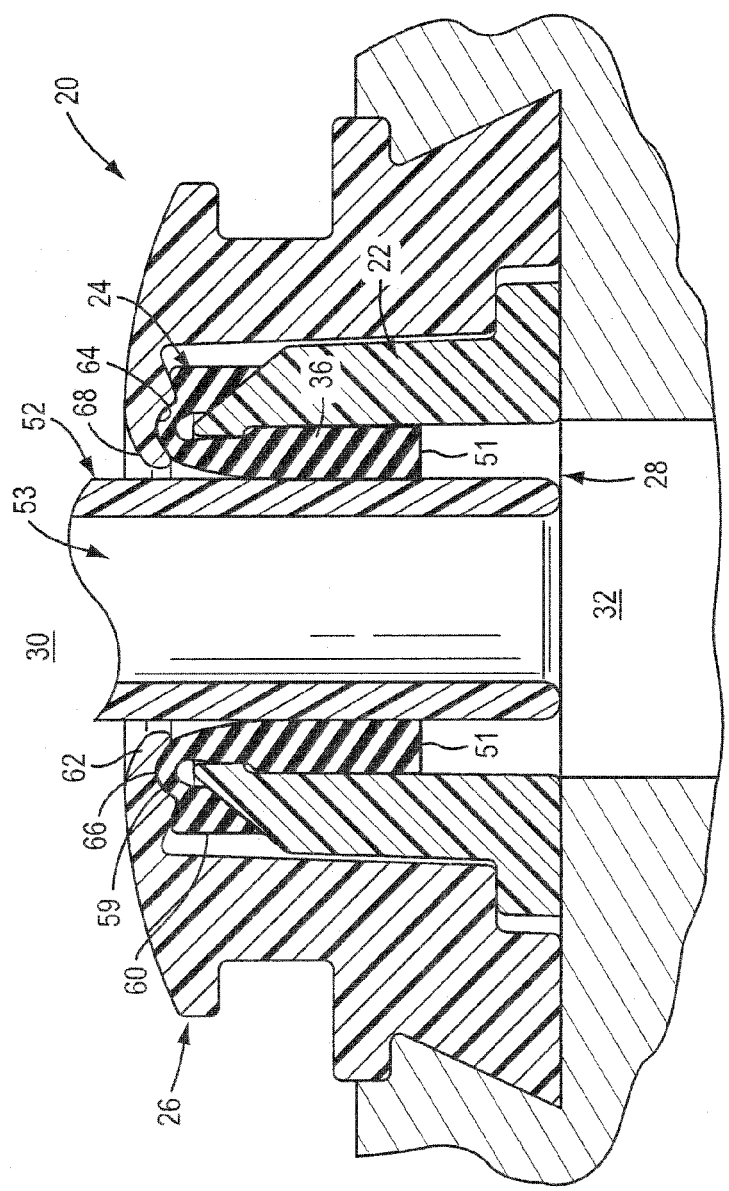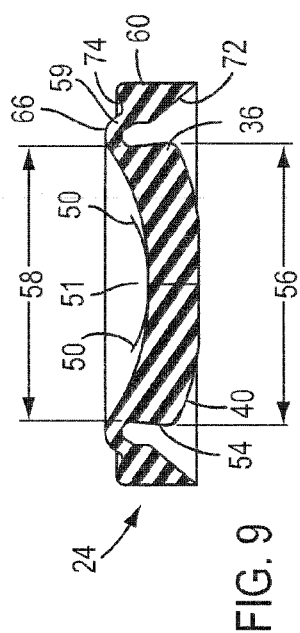
FIG. 8
FIG. 9

PORT CLOSURE SYSTEM FOR USE WITH A PROBE/FEED/DRAIN TOOL

CROSS-REFERENCE TO RELATED APPLICATIONS

Not Applicable.

FEDERALLY SPONSORED RESEARCH OR DEVELOPMENT

Not Applicable.

MICROFICHE/COPYRIGHT REFERENCE

Not Applicable.

FIELD OF THE INVENTION

The present invention relates generally to a system for accommodating the flow of a fluent substance. The invention more particularly relates to a port closure system having a flexible, resilient valve and accommodating a probe or feed/drain tool that directs the flow of a fluent substance through the valve.

BACKGROUND OF THE INVENTION

The inventor of the present invention has discovered that it would be advantageous to provide an improved system for retaining or otherwise mounting a flexible, resilient valve defining an initially closed orifice which can be opened to accommodate fluid flow through the valve, wherein the design of the system could provide advantages not heretofore contemplated in the industry or suggested by the prior art. In particular, the system of the present invention protects the resilient valve during insertion of a probe or feed/drain tool, assists in guiding the probe or feed/drain tool into proper engagement with the valve, maintains the proper alignment of the valve head during withdrawal of a probe or feed/drain tool from the valve, facilitates proper closing of the valve after portions of the valve have been forced away from their initially closed configuration, and is resistant to pressure differentials caused by a fluent substance acting against the valve.

One type of flexible, resilient, valve is a self-closing, slit-type valve mounted in a port of a fluent container. Such valves have a slit or slits which define a normally closed orifice that opens to permit flow therethrough in response to a probe, cannula or feed/drain tool inserted through the valve, or an increased pressure differential across the valve. Such valves are typically designed so that they automatically close to shut off flow therethrough upon removal of the probe, cannula or feed/drain tool or a reduction of the pressure differential across the valve.

Designs of such valves and of closures using such valves are illustrated in the U.S. Pat. No. 5,271,531, No. 5,927,566, and No. 5,934,512. Typically, the closure includes a body or base mounted on the container neck to define a seat for receiving the valve and includes a retaining ring or other structure for holding the valve on the seat in the base. See, for example, U.S. Pat. No. 6,269,986 and No. 6,616,016. The valve is normally closed and can withstand the weight of the fluid product when the bottle is completely inverted so that the liquid will not leak out unless the bottle is squeezed. With such an improved system, the lid or cap need not be re-closed (although it is typically re-closed if the package is to be transported to another location, packed in a suitcase, etc.). One approach to provide a valve with hydraulic hammer resistance is shown in commonly owned U.S. patent application Ser. No. 11/728,614, titled "DISPENSING VALVE WITH HYDRAULIC HAMMER RESISTANCE" and filed on Mar. 27, 2007 naming David J. Gaus et al as inventors, the entire disclosure of which is incorporated herein by reference. Other such valve systems for use with a probe or feed/drain tool are shown in commonly owned U.S. patent application Ser. No. 12/070,799, titled VALVE MOUNTING ASSEMBLY WITH SLIT MISALIGNMENT PREVENTION FEATURE, filed Feb. 21, 2008 and naming David J. Gaus as inventor, and U.S. patent application Ser. No. 12/268,814, titled PORT CLOSURE WITH HYDRAULIC HAMMER RESISTANCE, filed Nov. 11, 2008, and naming David J. Gaus as inventor, the entire disclosures of which are incorporated herein by reference.

While such valved systems have significant advantages and function well, it would be desirable to provide an improved system that includes multiple benefits with a minimal number of components.

SUMMARY OF THE INVENTION

In accordance with one feature of the invention, a port closure system includes a port to establish communication between an interior volume that can receive a fluent substance and an exterior environment, a valve including a flexible, resilient head extending across the port, and an annular flange located to extend over at least a portion of the valve head. The port has a laterally inwardly facing engaging surface. The valve head has an interior side facing the interior volume; an exterior side facing the exterior environment; at least one self-sealing slit through the head; confronting, openable portions along the slit to define a normally closed orifice in an unconstrained condition wherein the openable portions can move in a first direction toward the interior volume to an open orifice configuration and in a second direction toward the exterior environment to an open orifice configuration; and a laterally outwardly facing peripheral surface compressed laterally inwardly by engagement with the engaging surface of the port to thereby impose a closing force on the self-sealing slit to increase the resistance of the normally closed orifice to opening in at least the second direction when the valve head is subjected to a pressure differential acting across the valve head. The annular flange is located to extend over at least a portion the exterior side of the valve head to limit movement of the openable portions in the second direction.

In one feature, the interior side of the valve head is defined by an arcuate, convex surface.

According to one feature, the exterior side is defined by an arcuate, concave surface. In a further feature, the concave surface is semispherical.

As one feature, the at least one self-sealing slit includes two self-sealing slits extending transverse to each other.

According to one feature, the engaging surface of the port is a cylindrical surface with a diameter D, and the laterally outwardly facing peripheral surface of the valve head has a maximum diameter adjacent the interior side that in the unconstrained condition is greater than the diameter D. In a further feature, the laterally outwardly facing peripheral surface is a frusto-conical surface in the unconstrained condition.

In one feature, the system further includes a seat, and the valve further includes a peripheral attachment portion engaged in the seat.

As one feature, the system further includes a retention structure located to clamp the peripheral attachment portion between the retention structure and the seat, and the port is located within the retain structure.

In one feature, the system further includes a one-piece housing defining the seat and the annular flange. In a further feature, the retention structure is permanently fixed within the housing.

According to one feature, the valve further includes a flexible, resilient, intermediate portion extending from the peripheral attachment portion to the head, with the intermediate portion having an arcuate shaped exterior surface facing the exterior environment, and the annular flange having a surface overlying the exterior surface and shaped to conform to the arcuate shape of the exterior surface of the intermediate portion. In a further feature, the exterior surface of the intermediate portion is convex and the overlying surface of the annular flange has a conforming concave shape.

As one feature, the annular flange has an arcuate configuration in transverse cross section.

According to one feature, a flow of the fluent substance is provided via a probe that selectively penetrates the valve head, and the annular flange includes a probe directing surface sloped toward the valve head as the probe directing surface extends laterally inwardly.

Numerous other advantages and features of the present invention will become readily apparent from the following detailed description of the invention, from the claims, and from the accompanying drawings.

BRIEF DESCRIPTION OF THE DRAWINGS

In the accompanying drawings forming part of the specification, in which like numerals are employed to designate like parts throughout the same.

FIG. 8 is a section view taken from line 8-8 in FIG. 2 and showing the port closure system in a condition wherein a probe or feed/drain tool has been inserted into the port closure system; and FIG. 9 is a section view of a flexible resilient valve utilized in the port closure system.

DETAILED DESCRIPTION OF THE PREFERRED EMBODIMENT

Figure 1:
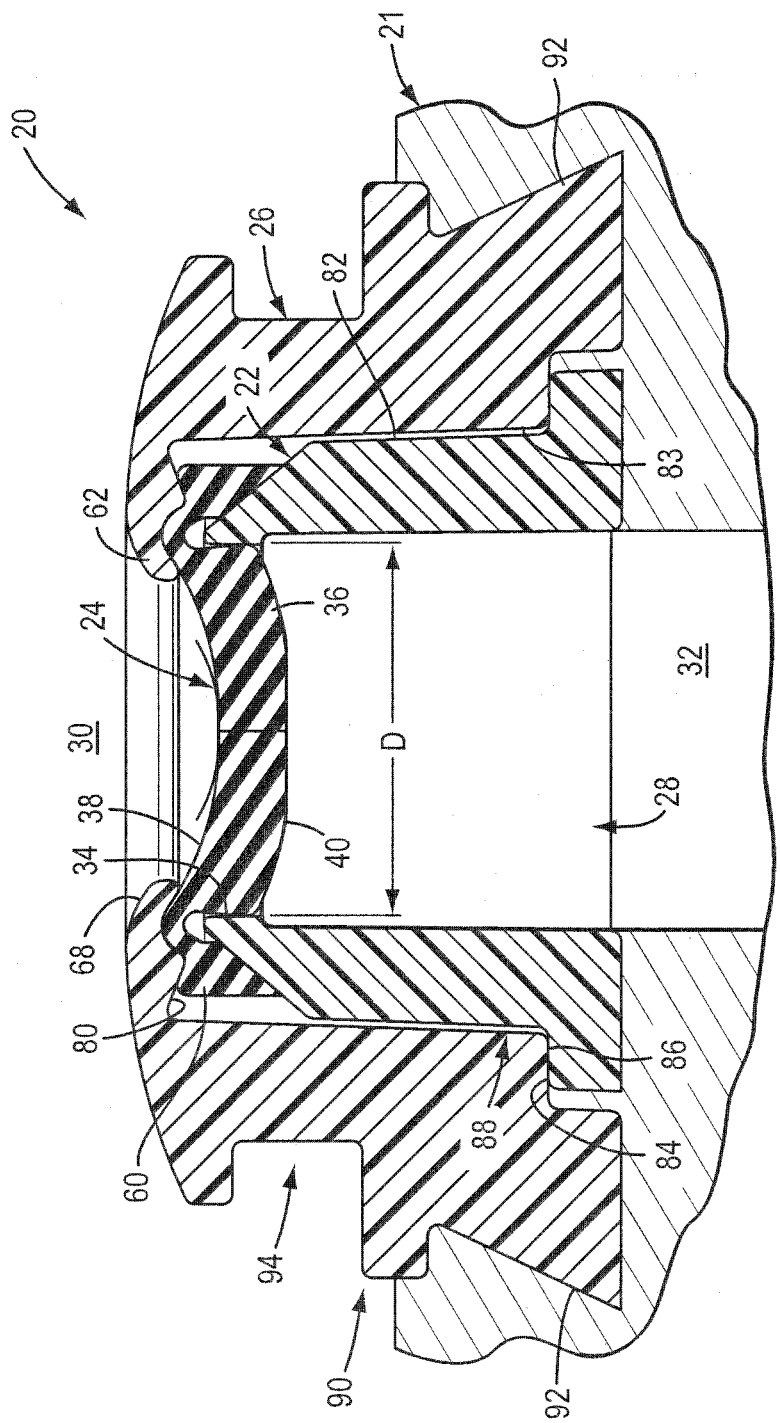
FIG. 1 is a section view showing a port closure system embodying the present invention with a fitment overmolded thereon.
Figure 2:
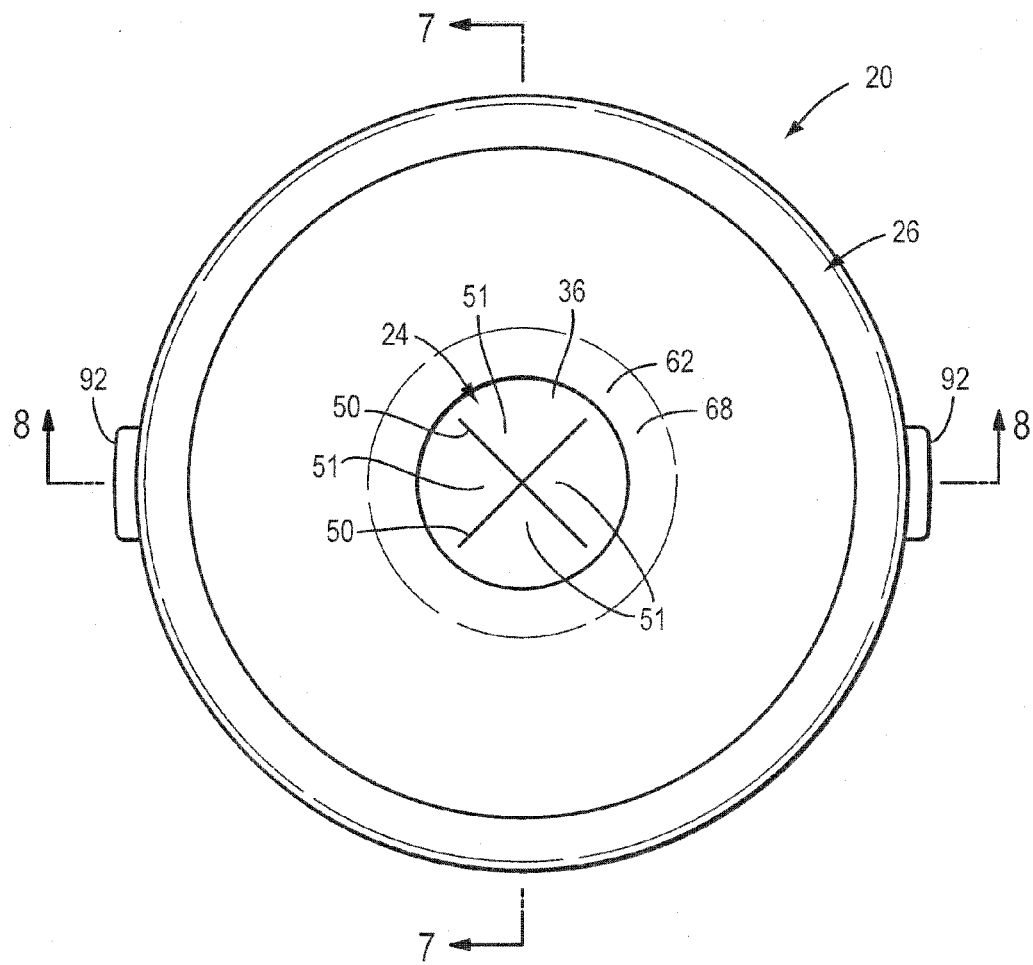
FIG. 2 is a plan view of the port closure system of FIG. 1, with overmolded fitment not shown.
Figure 3:
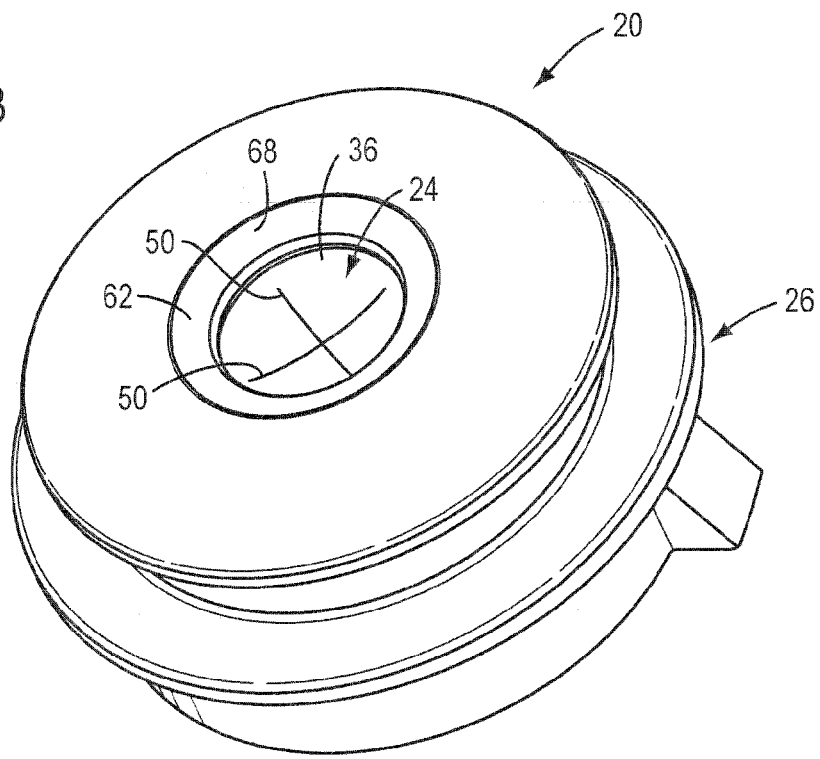
FIG. 3 is an isometric view from above of the port closure system.
Figure 4:
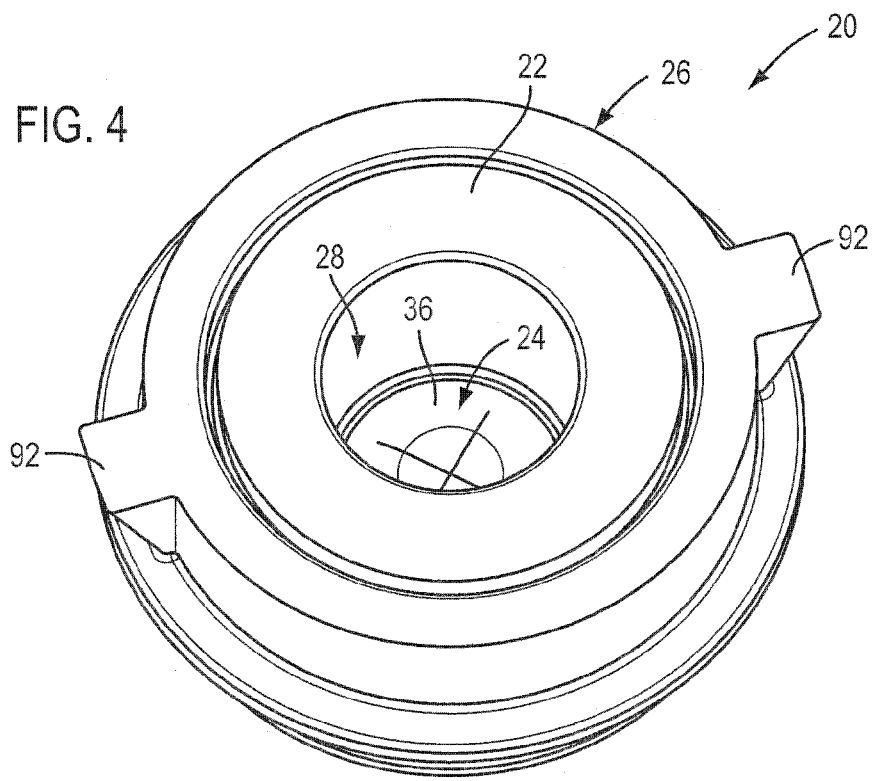
FIG. 4 is an isometric view from below of the port closure system.

While this invention is susceptible of embodiment in many different forms, this specification and the accompanying drawings disclose only one specific form as an example of the invention. The invention is not intended to be limited to the embodiment so described, however. The scope of the invention is pointed out in the appended claims.

As discussed in detail hereinafter, the port closure system of the present invention can be used to mount a valve in a fluid handling system, including in an enteral tube feeding system so as to accommodate transfer of fluent substances including, but not limited to, liquid feedings carrying essential nutrients. Further, the port closure system of the present invention can be used to mount a valve in an associated container or other dispensing structure so as to accommodate transfer of fluent substances including, but not limited to, water or other fluids suitable for consumption.

Notably, the present invention port closure system is especially suitable for use with the type of flexible, resilient valve that includes a peripheral attachment portion of the valve and a central valve head (which is often openable in either of two opposite directions).

For ease of description, many of the figures illustrating the invention show one form of a valve held in one embodiment of the present invention port closure system in one typical orientation that the port closure system may have in a particular application, and terms such as upper, lower, horizontal, etc., are used with reference to this orientation. It will be understood, however, that the port closure system of this invention may be manufactured, stored, transported, sold, and used in an orientation other than the orientation described.

The port closure system of the present invention may be used with a variety of conventional or special fluent substance handling and/or holding systems, including tube fitment housings, glass or plastic bottles, flexible tubular containment structures, containers, tanks, vessels, and other equipment or apparatus, the details of which, although not fully illustrated or described, would be apparent to those having skill in the art and an understanding of such systems. The particular fluent substance handling or holding system, per se, forms no part of, and therefore is not intended to limit, the broad aspects of the present invention. It will also be understood by those of ordinary skill that novel and non-obvious inventive aspects are embodied in the described exemplary valve mounting system alone.

A presently preferred embodiment of the port closure system is illustrated in FIGS. 1-8 and is designated generally by the number 20. The system 20 is illustrated in connection with a fluent system in the form of a tube fitment housing, only partially shown at 21, that can be connected to an enteral feeding tube or system. The system 20 allows the selective introduction of liquid feeding that supply critical nutrients to a patient via the enteral feeding tube or system, while maintaining a closed and lock free condition for the enteral feeding tube or system when a liquid feeding is not being provided to a patient.

Figure 5:
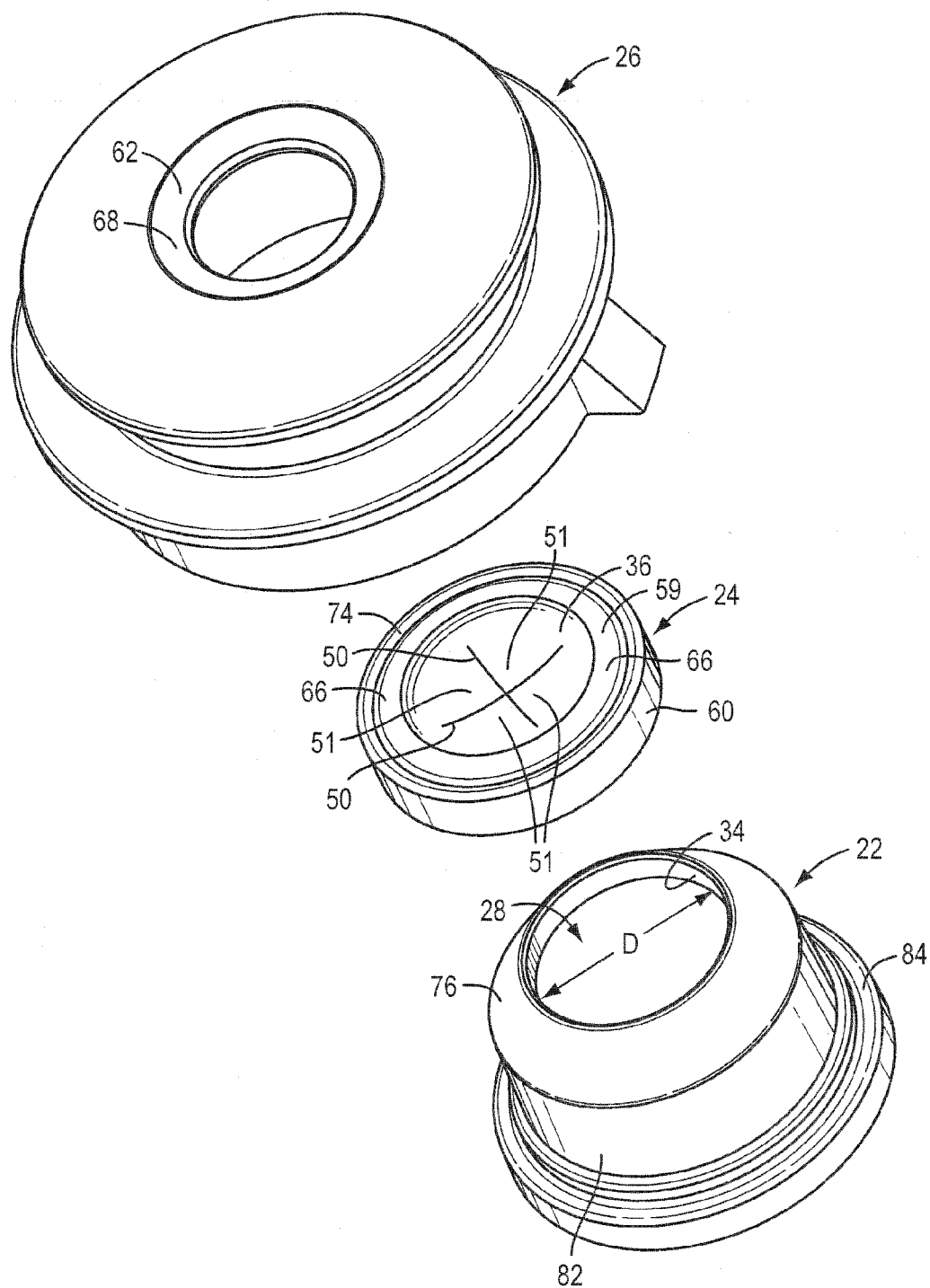
FIG. 5 is an exploded isometric view of the port closure system system taken from above.

As best seen in FIG. 1, the system 20 includes a retention structure 22, a valve 24, and a one-piece housing or mounting fitment 26. The retention structure 22 includes a port 28 for establishing communication between an exterior environment 30 and interior volume 32 that can receive a fluent substance such as a liquid feeding. As best seen in FIGS. 1, 5 and 7A, the port 28 has a laterally inwardly facing engaging surface 34 that is preferably cylindrical with a diameter D.

Figure 6:
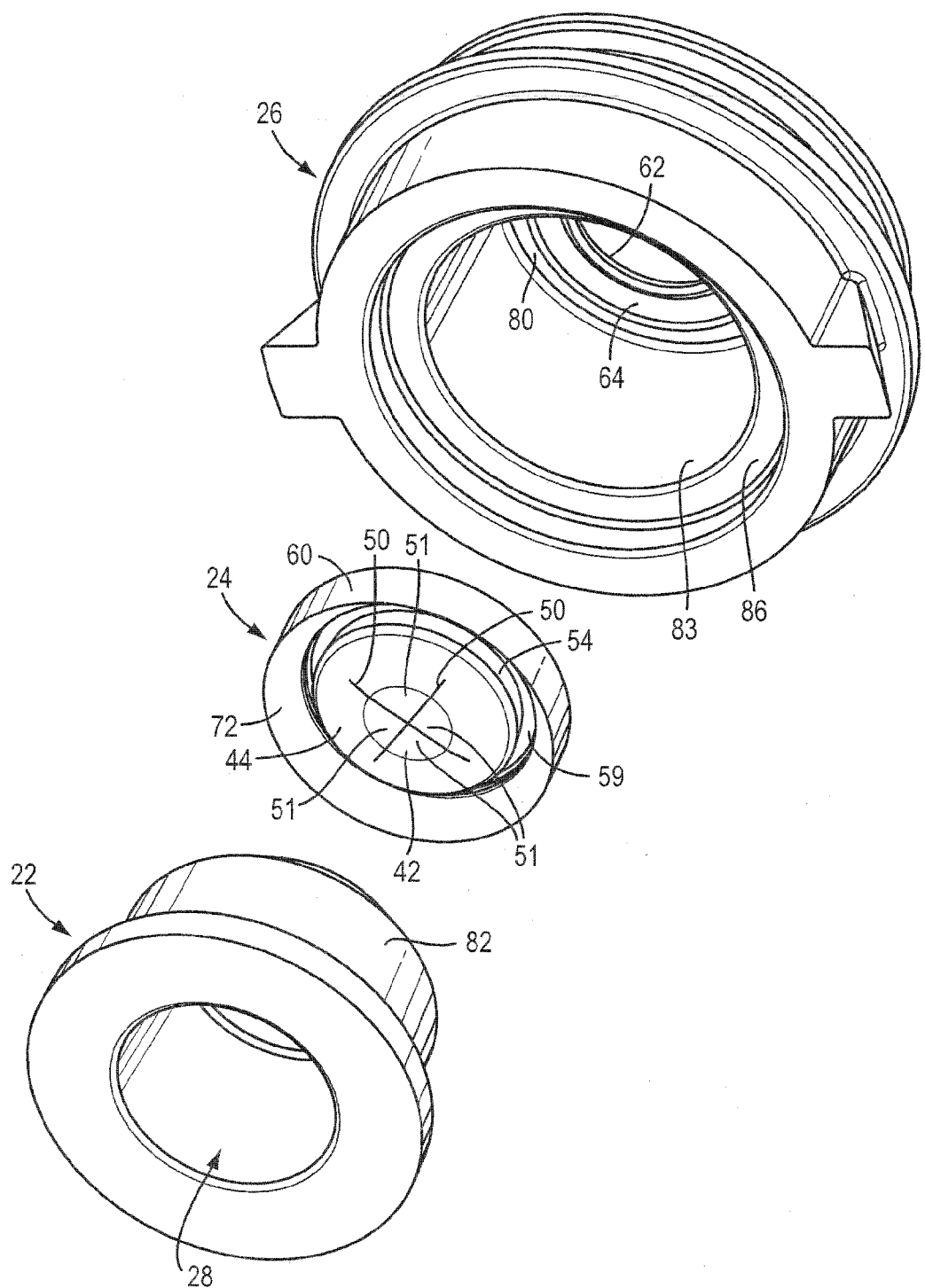
FIG. 6 is an exploded isometric view of the port closure system taken from below.

The valve 24 is a self-closing, slit-type valve and can be seen in greater detail in FIGS. 5, 6, and 9. The valve 24 is preferably molded as a unitary structure from material which is flexible, pliable, elastic, and resilient. This can include elastomers, such as a synthetic, thermosetting polymer, including silicone rubber, such as the silicone rubber sold by Dow Corning Corp. in the United States of America under the trade designation C6-560. Another suitable silicone rubber material is sold in the United States of America under the designation Wacker 3003-60 by Wacker Silicone Company. Both of these materials have a hardness rating of 60 Shore A. The valve 24 could also be molded from other thermosetting materials or from other elastomeric materials, or from thermoplastic polymers or thermoplastic elastomers, including those based upon materials such as thermoplastic propylene, ethylene, urethane, and styrene, including their halogenated counterparts.

Figure 7:
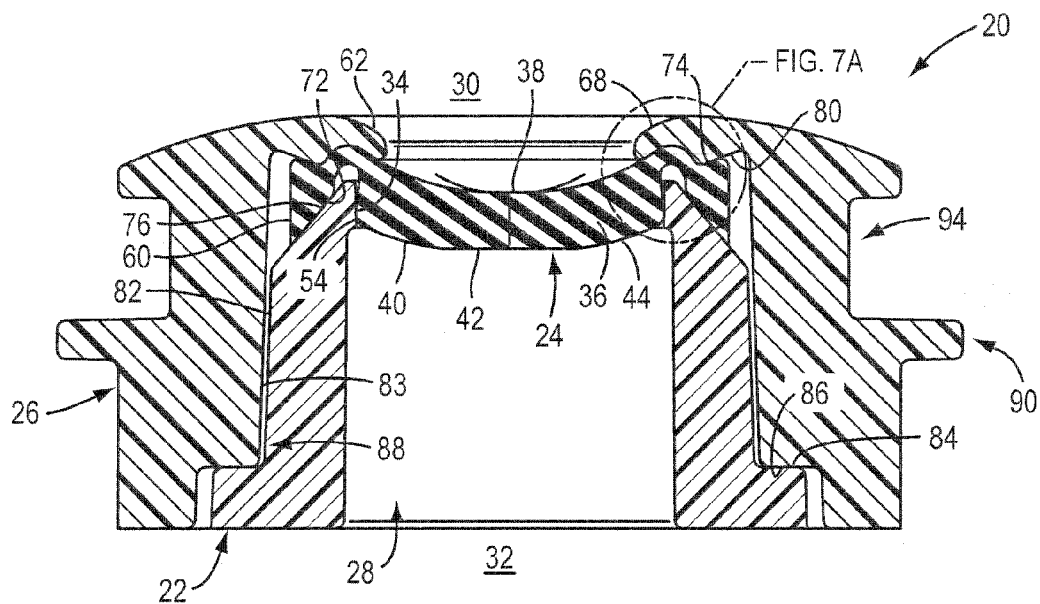
FIG. 7 is a section view taken from line 7-7 in FIG. 2.
Figure 7A:
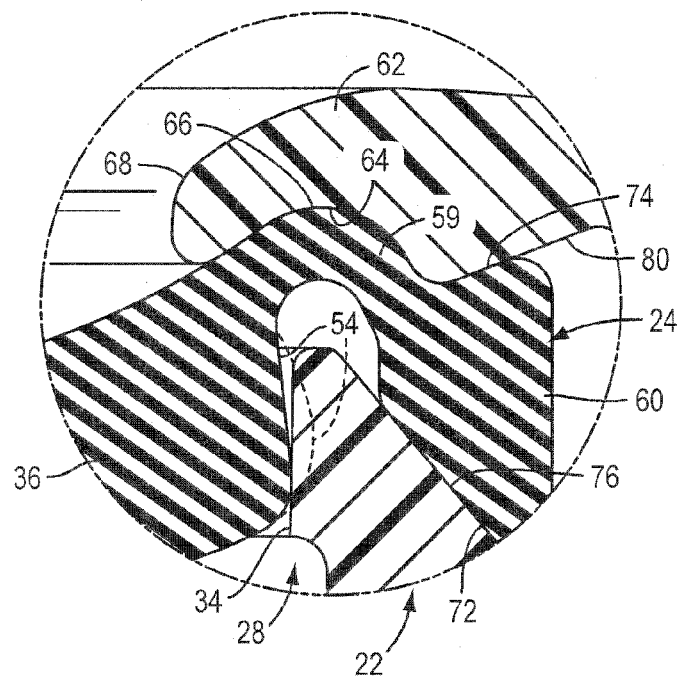
FIG. 7A is an enlarged view of the area encircled by arrow "A"

The valve 24 has a normally closed, rest position or configuration shown in FIGS. 1-7 and 9. The valve 24 is typically designed to remain closed when the pressure differential across the valve head 36 is below a predetermined amount. The inherent resiliency of the valve 24 allows the valve 24 to return to the normally closed condition (by action of the force generated from the resilient valve's deformational stresses). The valve 24 can be forced to one or more open positions or configurations, as shown in FIG. 8 when a sufficiently high force acts on the valve 24 as described hereinafter. As best seen in FIG. 7, the valve 24 includes a flexible, central portion or head 36 that extends laterally across the port 28, with a first or exterior side 38 and a second or interior side 40. When the valve 24 is closed, the interior side 40 has a surface that is convex and arcuate in shape, and the exterior side 38 has a surface that is concave and arcuate in shape with a planar central portion 42 and a semispherical outer portion 44. In this regard, while preferred forms of valve 24 and the head 36 are shown herein, it should be understood that other configurations, such as for example those shown in aforementioned U.S. patent application Ser. Nos. 11/728,614 and 12/070,799 may be desirable depending upon the specific parameters and requirements of each particular application.

As best seen FIGS. 1-7, the head 36 has planar, intersecting, self-sealing slits 50 which together define a closed orifice when the valve 24 is closed. Preferably, the slits 50 are normal to each other and equal in length. In the illustrated forms of the valve 24, the slits 50 define four, generally sector-shaped, equally sized flaps or petals 51 in the head 36. The flaps or petals 51 may be also characterized as "openable regions" or "openable portions" of the valve head 36. Each flap or petal 51 has a pair of diverging transverse faces defined by the slits 50, and each transverse face seals against a confronting transverse face of an adjacent petal 51 when the valve 24 is closed.

The valve 24 can be molded with the slits 50. Alternatively, the valve slits 50 can be subsequently cut into the head 36 of the valve 24 by suitable conventional techniques. As another alternative, the slits 50 could be partially molded into the head 36, with the remainder being cut after molding. However the slits 50 are formed, the orifice should be closed when the valve 24 is in an unconstrained or as-molded condition. In operation, the petals 51 can be forced open inwardly in a first direction (toward the interior volume 32 in FIGS. 1, 7 and 8) from the intersection point of the slits 50 when a sufficient force (or pressure differential) is applied to the exterior side 38 of the valve head 36, or forced open outwardly in a second direction (toward the exterior environment 30 in FIGS. 1, 7 and 8) from the intersection point of the slits 50 when a sufficient force (or pressure differential) is applied to the interior side 40 of the head 36.

FIG. 8 illustrate an example of the valve 24 opening in the first direction wherein a probe or cannula in the form of a fluid inlet conduit or feed tool 52 has been inserted in the first direction in order to direct a liquid feed into the interior volume 32 via a flow path 53 in the feed tool 52. The open petals 51 accommodate the penetration of the end of the feed tool 52 into the interior volume 32 of the fitment 21. The petals 51 seal around the cylindrical periphery of the feed tool 52 in a substantially liquid-tight manner. When the feed tool 52 is withdrawn from the valve head 36 by movement in the second direction, the inherent resiliency of the head 36 and petals 51 return the orifice to the closed condition.

As best seen in FIGS. 6, 7A and 9, the valve head 36 may also be characterized as having a laterally outwardly facing peripheral surface 54 at the outer periphery of the valve head 36. The surface 54 is sized and/or shaped in its as-molded or unconstrained condition so that it is compressed laterally inwardly by engagement with the surface 34 of the port 28, as best seen in FIGS. 7 and 7A, with the phantom line in FIG. 7A showing the unconstrained size and shape of surface 54 of the illustrated embodiment in comparison to the surface 34. This laterally inward compression of the head 36 imposes a closing force on the self-sealing slits 50 that increases the resistance of the normally closed orifice to opening in at least the second direction toward the exterior environment 30 when the valve head 36 is subjected to an increased pressure differential acting across the head 36, such as may be caused by gastric gases generated within a patient and acting through an enteral feed tube or system. It should be noted that this is particularly advantageous in connection with a system 20 wherein the valve head 36 is penetrated by a feed tool 52 and must return to the closed condition and resist pressure differentials after the feed tool 52 is removed.

With respect to the laterally inward compression of the head 36, as best seen in FIG. 9, in the preferred, illustrated form, the surface 54 is slightly frusto-conical with a maximum diameter 56 adjacent the interior side 40 and a minimum diameter 58 adjacent a flexible, resilient intermediate portion 59 of the valve 24 that connects the head 36 to a peripheral attachment portion or flange 60 of the valve 24. The maximum diameter 56 is greater than the diameter D of the surface 34. The minimum diameter 58 is preferably equal to the diameter D of the surface 34, or just slightly less than the diameter D. While it is believed that the illustrated shape provides a superior closing force, other shapes and/or sizes for the surface 54 that create an interference fit with the surface 34 further may be desirable depending upon the particular requirements and parameters of each application.

The port closure system 20 further includes an annular flange 62 that is located to extend over at least a portion of the exterior side 38 of the valve head 36 to limit movement of the valve head 36 and its petals 51 in the second direction toward the exterior environment 30. As best seen in FIGS. 7A and 8, the annular flange 62 includes a surface 64 facing the intermediate portion 59 of the valve 24, with the surface 64 being shaped to conform to the shape of the intermediate portion 59. In this regard, it is preferred that the intermediate portion 59 have an arcuate shape including a convex exterior surface 66 facing the surface 64 of the flange. The flange 62 and surface 64 limit movement of the petals 51 and the head 36 in the second direction and further help to prevent misalignment of the slits 50 and petals 51 as the head 36 moves from an open condition to a closed condition. It is believed that these features combine with the previously described features that provide laterally inward compression of the head 36 to provide a movement of the valve head 36 from the open condition to the closed condition as the feed tool 52 is withdrawn from the system 20 and maintenance of the closed condition of the valve 24 after withdrawal of the feed tool 52 that are superior to conventional and known port closure systems.

As an additional feature, it is also preferred that the flange 62 include a probe directing surface 68 that is sloped toward the valve head 36 as the probe directing surface 68 extends laterally inwardly, as best seen in FIGS. 1, 7 and 8. The surface 68 helps to direct a probe, such as the feed tool into proper alignment with the valve 24 and the head 36, while also protecting the valve 24 and the head 36 from damage that can be caused by improper insertion of the feed tool 52.

To accommodate mounting and retention of the valve 24, the flange 60 preferably has a generally dovetail-shaped, transverse cross section which defines a pair of frusto-conical surfaces 72 and 74, as best seen in FIG. 9. As best seen in FIGS. 5 and 7, the retention structure 22 includes a frusto-conical surface 76 for matingly engaging the axially inwardly facing frusto-conical surface 72 of the flange 60. As best seen in FIGS. 6 and 7, the mounting fitment 26 includes an axially inwardly facing frusto-conical seat 80 which is adapted to matingly engage, and clamp against, the axially outwardly facing frusto-conical surface 74 of the flange 60. The retention structure 22 further includes a radially outwardly facing cylindrical wall 82 that is received in a cylindrical opening 83 of the mounting fitment 26, with a pair of engaging shoulder surfaces 84 and 86 on the retention structure 22 and mounting fitment 26, respectively, to limit the axial engagement of the retention structure 22 into the mounting fitment 26 so as to provide the appropriate clamping force on the flange 60. Preferably, the retention structure 22 is permanently fixed or bonded within the mounting fitment 26, preferably, via ultrasonic welding in an annular zone adjacent the shoulders, as indicated at 88.

While a preferred form of mounting has been shown, the retention structure 22, valve 24 and fitment 26 could have other configurations, such as a different shape for the flange 60 and seat 80. Also, in some other arrangements, the valve 24 could be held in the mount fitment 26 by other means, such as, for example, the valve 24 could be held in by heat bonding, adhesive, and/or a press fit, etc. with or without the flange 60 and/or intermediate portion 59. As another alternative, the valve 24 could be bi-injection molded onto one of the retention structures 22 and/or the mount fitment 26.

With reference to FIG. 7, the mount fitment 26 has a laterally outwardly facing profile 90 to be dictated primarily by the requirements of each application. Accordingly, the details of the profile 90 are not critical to the inventive concepts herein. It should be noted that the profile includes a pair of oppositely spaced tabs 92 (best seen in FIGS. 2 and 4) that allow for the system 20 to be properly located with respect to the assembly of the fitment housing 21. It is also worth noting that the profile 90 includes an annular channel or recess 94 that allows a snap-type connection with other components of the enteral feeding system.

It is to be understood that the orifice of the valve 24 may be defined by structures other than the illustrated straight slits 50. The slits may have various different shapes, sizes and/or configurations in accordance with the requirements and parameters of each particular application. For example, the orifice may also include four or more intersecting slits.

If it is desired to provide particular performance characteristics, then the system 20 is preferably configured for use in conjunction with (1) the characteristics of the particular application, which, for example, may establish the maximum anticipated pressure differential across the valve 24; (2) the characteristics of the particular substance or product to be used with the system 20; and (3) any relevant characteristics of the other components, such as the feed tool or cannula 52. For example, the viscosity and density of the fluent substance can be relevant factors in designing the specific configuration of the system 20 and valve 24. The rigidity and durometer of the valve material, and size and shape of the valve head 36, can also be relevant to achieving some desired characteristics, and can be selected for accommodating the normal range of pressure differential that is expected to be typically applied across the valve head 36, and for accommodating the characteristics of the substance to be used with the system 20.

It should be appreciated that the system 20 can maintain a leak-free seal between the exterior environment 30 and the interior 32 of the enteral feeding tube or system, thereby allowing for elimination of an overcap as required in some current systems. In this regard, the radially inward compressive forces created by the interference between the valve head 36 and the retention structure 28 serve to ensure proper closing of the valve 24 and maintaining of the valve 24 in its closed position, while the annular flange 62 helps to prevent outward movement of the valve head 36 and misalignment of the valve petals 51 as the cannula or feed tool 52 is removed.

It should be appreciated that while the system 20 has been described herein in connection with an enteral feeding tube or system and/or in connection with a probe/feed/drain tool or cannula 52, the system 20 may find use in other applications and that no limitation to use with an enteral feeding tube or system and/or a probe/feed/drain tool or cannula 52 is intended unless expressly recited in the claim(s).

It will be readily observed from the foregoing detailed description of the invention and from the illustrations thereof that numerous other variations and modifications may be effected without departing from the true spirit and scope of the novel concepts or principles of this invention.

The invention claimed is:
1. A port closure system (20), said system comprising:
a port (28) to establish communication between an interior volume (32) that can receive a fluent substance and an exterior environment (30), the port (28) having a laterally inwardly facing engaging surface (34);
a valve (24) including a flexible, resilient head (36) extending across the port (28), the head (36) having:
an interior side (40) facing the interior volume (32);
an exterior side (38) facing the exterior environment (30);
at least one self-sealing slit (50) through the head (36);
confronting, openable portions (51) along the slit (50) to define a normally closed orifice in an unconstrained condition wherein the openable portions (51) can move in a first direction toward the interior volume (32) to an open orifice configuration and in a second direction toward the exterior environment (30) to an open orifice configuration; and
a laterally outwardly facing peripheral surface (54) compressed laterally inwardly by engagement with the engaging surface (34) to thereby impose a closing force on said self-sealing slit (50) to increase the resistance of the normally closed orifice to opening in at least the second direction when the valve head (36) is subjected to a pressure differential acting across the valve head (36); and
an annular flange (62) located to extend over at least a portion the exterior side (38) of said valve head (36) to limit movement of the openable portions (51) in the second direction.

2. The system (20) of claim 1 wherein the interior side (40) is defined by an arcuate, convex surface (44).

3. The system (20) of claim 1 wherein the exterior side (38) is defined by an arcuate, concave surface (38).

4. The system (20) of claim 3 wherein the concave surface (38) is semi spherical.

5. The system (20) of claim 1 wherein the at least one self-sealing slit (50) comprises two self-sealing slits (50) extending transverse to each other.

6. The system (20) of claim 1 wherein the engaging surface (34) is a cylindrical surface with a diameter D and the laterally outwardly facing peripheral surface (54) has a maximum diameter (56) adjacent the interior side (40) that in the unconstrained condition is greater than the diameter D.

7. The system (20) of claim 6 wherein the laterally outwardly facing peripheral surface (54) is a frusto-conical surface in the unconstrained condition.

8. The system (20) of claim 1 further comprising a seat (80) and wherein the valve (24) further comprises a peripheral attachment portion (60) engaged in said seat (80).

9. The system (20) of claim 8 further comprising a retention structure (22) located to clamp the peripheral attachment portion (60) between the retention structure (22) and the seat (80), and wherein the port (28) is located within the retention structure (22).

10. The system (20) of claim 9 further comprising a one-piece housing (26) defining said seat (80) and said annular flange (62).

11. The system (20) of claim 10 where said retention structure (22) is permanently fixed within said housing (26).

12. The system (20) of claim 8 wherein said valve (24) further includes a flexible, resilient, intermediate portion (59) extending from said peripheral attachment portion (60) to said head (36), the intermediate portion (59) having an arcuate shaped exterior surface (66) facing the exterior environment (30), and the annular flange (62) having a surface (64) overlying the exterior surface (66) and shaped to conform to the arcuate shape of the exterior surface (66) of the intermediate portion (59).

13. The system (20) of claim 12 wherein the exterior surface (66) of the intermediate portion (59) is convex and the overlying surface (64) of the annular flange (62) has a conforming concave shape.

14. The system (20) of claim 1 wherein said annular flange (62) has an arcuate configuration in transverse cross section.

15. The system (20) in accordance with claim 1 wherein a flow of said fluent substance is provided via a probe (52) that selectively penetrates said valve head (36), and said annular flange (62) includes a probe directing surface (68) sloped toward said valve head (36) as said probe directing surface (68) extends laterally inwardly.

* * * * *